(12) United States Patent
Heller et al.

(10) Patent No.: US 7,879,610 B1
(45) Date of Patent: *Feb. 1, 2011

(54) ELECTROPORATION SYSTEM AND METHOD FOR FACILITATING ENTRY OF MOLECULES INTO CELLS IN VIVO

(75) Inventors: Richard Heller, Temple Terrace, FL (US); Mark J. Jaroszeski, Tampa, FL (US); Richard Gilbert, Tampa, FL (US)

(73) Assignee: University of South Florida, Tampa, FL (US)

( * ) Notice: Subject to any disclaimer, the term of this patent is extended or adjusted under 35 U.S.C. 154(b) by 446 days.

This patent is subject to a terminal disclaimer.

(21) Appl. No.: 10/907,631

(22) Filed: Apr. 8, 2005

Related U.S. Application Data

(63) Continuation-in-part of application No. 09/939,518, filed on Aug. 24, 2001, now Pat. No. 7,713,740.

(51) Int. Cl.
*C12N 15/87* (2006.01)
*A61N 1/30* (2006.01)

(52) U.S. Cl. .................................... 435/461; 604/20
(58) Field of Classification Search ............... 435/461; 604/20
See application file for complete search history.

(56) References Cited

U.S. PATENT DOCUMENTS

| 6,055,453 | A  | * | 4/2000  | Hofmann et al. | 604/21  |
| 6,678,558 | B1 | * | 1/2004  | Dimmer et al.  | 607/3   |
| 6,800,484 | B2 | * | 10/2004 | Nolan et al.   | 435/461 |

* cited by examiner

*Primary Examiner*—J. E Angell
(74) *Attorney, Agent, or Firm*—Michael M. McGaw; Smith & Hopen, P.A.

(57) ABSTRACT

A method for facilitating a delivery of a molecule into an interior space of a cell includes the steps of introducing a molecule into a target tissue comprising a cell and applying a substantially continuous low-level electric field to the target tissue. The field is applied for a duration sufficient to effect a change in porosity the cell of the target tissue sufficient to facilitate an entry of a desired molecule into an interior of the cell.

10 Claims, No Drawings

ELECTROPORATION SYSTEM AND METHOD FOR FACILITATING ENTRY OF MOLECULES INTO CELLS IN VIVO

CROSS REFERENCE TO RELATED APPLICATION

This application is a continuation-in-part and claims priority to U.S. patent application Ser. No. 09/939,518 filed Aug. 24, 2001 by the same inventors entitled: "Method of Using Electric Fields to Facilitate the Entry of Molecules into Cells in Vivo."

FIELD OF INVENTION

This invention relates to the use of an electric field to affect the delivery of a molecule to a target tissue site and facilitate the uptake of a molecule by a cell.

BACKGROUND OF THE INVENTION

Most therapeutic molecules require delivery to a living cell by some means in order to effect a response. Standard therapies include oral administration or other techniques to introduce a treatment molecule into the system. However, even with a therapeutic molecule in the vicinity of a cell, the cell membrane can partially or completely block the uptake ~f that molecule into the cell itself. To overcome this, many methods have been developed; one such method is the use of electric fields to facilitate passage of the molecules from the extracellular space to the intracellular space.

Scientific research has led to the current understanding that exposure of cells to intense electric fields for brief periods of time temporarily destabilizes membranes. This effect has been described as a dielectric breakdown due to an induced transmembrane potential, and was termed "electroporation," or "electropermeabilization," because it was observed that the molecules. that do not normally pass through the membrane gain intracellular access after the cells were treated with electric fields. The porated state was noted to be temporary, with the cells typically remaining in a destabilized state on the order of a few minutes after the cessation of the electrical fields.

The physical nature of electroporation makes it universally applicable. A variety of in vivo procedures utilize this type of treatment to gain temporary access to the cytosol. These include the delivery of drugs to cells within tissues and the delivery of DNA to cells within tissues. A notable example of loading molecules into cells in vivo is electrochemotherapy. The procedure utilizes a drug combined with electric pulses as a means for loading tumor cells with an anticancer drug, and has been performed in a number of animal models and in clinical trials (see, for example, Heller et al., Cancer 77, 964-71, 1996). Also, plasmid DNA has been loaded into rat liver cells (Heller et al., FEBS Left. 389, 225-28, 1996), murine tumors (Niu et al., Cancer Research 59, 5059-63, 1999), rat hepatocellular carcinomas (Heller et al." Gene Therapy 7,826-29, 2000}, and murine skin in vivo [Heller et al., DNA and Cell Biology20(1}, 21-26, 2001].

The loading of molecules by electroporation in vivo is typically, but not necessarily, carried out by first exposing the cells (located within a tissue) of interest to the molecule to be loaded. This is accomplished by placing the molecules of interest into the extracellular space by injection, jet injection, transdermal delivery, infusion into tissue or blood vessel, or other means known in the art. The cells are then exposed to electric fields by administering one or more direct current pulses. Pulsed electric fields are normally applied using an electrical generator and electrodes that contact or penetrate a region of tissue, which allows electrical energy to be transmitted to the cells of interest. Electrical treatment is typically, but not necessarily, conducted in a manner that results in a temporary membrane destabilization with minimal cytotoxicity.

The intensity of electrical treatment is described by the magnitude of the applied electric field. This field is defined as the voltage applied to the electrodes divided by the distance between the electrodes. Generally, electric field strengths ranging from 100 to 5000V/cm have been used; this range has been dictated by the need to interfere with the cell membrane to effect the uptake of the molecular species desired. In addition, the field strength is also a function of the type of tissue to be treated, with some requiring higher fields owing to their specific natures.

High field strengths, 100V/cm and greater, were used exclusively in the past. The duration of the applied fields is an important factor, and the relationship between field strength and duration is critical. The current state of the art utilizes high electric field strengths to effect the membrane change and requires pulse durations that are very brief in order to achieve molecular delivery. The concept of very long pulse durations (greater than 100 ms) has heretofore never been used with respect to the field strength, enabling in vivo molecular delivery using almost insignificant electric fields. In fact, the converse was held to be true by practitioners of the art; operating parameters with short-duration high fields being held as the only way to achieve electroporation. The pulsed electric fields used for molecule delivery are generally rectangular in shape; however, exponentially decaying pulses and bipolar pulses have also been used. Molecular loading has been performed with pulse widths ranging from microseconds to milliseconds. The number of pulses delivered typically has ranged from one to eight, with multiple pulses being applied during the course of a treatment.

Work related to the manipulation of the parameters influencing electroporation devices has been the subject of many articles and patents. One such patent, U.S. Pat. No. 6,241,701 to Hoffmann, describes electric field intensities ranging from 25 to 1300 V/cm with times or pulse widths ranging from 10 µs to about 100 ms. The effectiveness of these ranges is described as a correlation between high fields for short duration versus low fields with a preferred longer pulse width. From the statements contained in Hoffmann, one would be led to manipulate the parameters equally with respect to each other, since they are described as being equal in importance. There is no suggestion to vary one parameter namely, the pulse width, to be greater in a nonlinear fashion with respect to the field strength; in addition, there is no teaching to extend the pulse width to any time greater than 100 ms.

SUMMARY OF INVENTION

It is therefore an object of the invention to provide a system and method for facilitating a delivery of a molecule into an interior space of a cell.

It is a further object to provide such a system and method incorporating low electric fields and long pulse durations.

These and other objects are achieved by the present invention, a first aspect of which comprises a method for facilitating a delivery of a molecule into an interior space of a cell. The method comprises the steps of introducing a molecule into a target tissue comprising a cell and applying a substantially continuous low-level electric field to the target tissue. The field is applied for a duration sufficient to effect a change in porosity in the cell of the target tissue sufficient to facilitate an entry of a desired molecule into an interior of the cell.

The invention further comprises a system for facilitating a delivery of a molecule into an interior space of a cell. The system comprises means for introducing a molecule into a target tissue comprising a cell and means for applying a substantially continuous low-level electric field to the target tissue. The applying means comprises means for applying the field for a duration sufficient to effect a change in porosity the cell of the target tissue sufficient to facilitate an entry of a desired molecule into an interior of the cell.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read.

DETAILED DESCRIPTION OF THE PREFERRED EMBODIMENT

A description of the preferred embodiments of the present invention will now be presented.

As described above, the electric field strength and pulse duration of the instant invention provide for a facilitation of the delivery of a molecule to a target cell, as effected by a low-voltage electric field with increasing application times or pulse widths. For example, within some field strength ranges, the application time or pulse width will be orders of magnitude higher than previously described, although this is not intended as a limitation.

For the purpose of this invention, a pulsed electric field is defined as the electric field resulting from an application of an electric waveform such as rectangular or exponentially decaying waveform. The pulsed electric fields comprise a variety of shapes, including, but not limited to, square, rectangular, exponentially decaying, exponentially increasing, bipolar, or sinusoidal pulses, or any combination of the foregoing and including nongeometrically characterizable shapes, with or without AC and DC offset (bias) voltages. The foregoing list of waveforms also is intended to include waveforms that can be characterized by mathematical functions or mathematical approximations.

The characteristics of the field, used to facilitate the entry of the molecules into the target cell include field strengths between 1 mV/cm and 200 V/cm, applied as pulses of substantially continuous energy. The duration of the pulse ranges from 0.1 s to 20 minutes, with 100 ms 100 s being a preferred range. A single pulse may be applied or a plurality of sequential pulses, either of the same magnitude or differing magnitudes of duration and field strength. A preferred pulse duration range has been found to be actually approximately exponentially greater than those suggested by the prior art in some ranges, and greatly exceeds any known to have been reported to date. In fact, the present inventors have discovered that by using a longer pulse duration, the field strength needed to effect facilitation of molecular delivery may be significantly lowered. As a result, fewer deleterious effects of the procedure are experienced, since the electric field imposition is more a function of time rather than field strength.

The tissues to which this method may be applied include, but are not intended to be limited to, skin, tumor, skeletal muscle, smooth muscle, blood, blood vessel, brain, lymph, liver, pancreas, bone, colon, small intestine, cardiac, lung, breast, testes, prostate, and cornea. In fact, any living species that uses gas transfer in its metabolic processes may be used as a target tissue, including, but not limited to: animals, plants, fish, various insect species, reptiles, .etc.

The magnitude of the electric fields applied are selected based on the susceptibility of the particular tissue to the pulses, and the corresponding pulse durations are a function of the resistivity of the type of tissue to temporary electrical damage. Representative parameters for a few types of tissue are contained in Table 1.

TABLE 1

| Tissue | Range of Field Parameters | Preferred Duration Range | Preferred Strength Range |
|---|---|---|---|
| Muscle | 1 µs-100 s<br>1 mV/cm-100,000 V/cm | 100 ms-10 s | 1 mV/cm-400 V/cm |
| Skin | 1 µs-100 s<br>1 mV/cm-10,000 V/cm | 100 ms-10 s | 1 mV/cm-500 V/cm |
| Tumor | 1 µs-100 s<br>1 mV/cm -10,000 V/cm | 100 ms-10 s | 1 mV/cm-800 V/cm |

As shown in Table 1, the pulse width is believed to comprise a critical factor in the method of the present invention.

The means for introducing the molecule of interest into the target tissue may comprise a technique selected from a group consisting of traditional syringe injection, jet injection, oral dosing, or other means as known in the art. In addition, the molecule of interest may also be caused to move to the target tissue by means of other electric pulses or by other means known in the art. The molecule of interest may also be dissolved, suspended, or emulsified in an appropriate carrier.

A subject molecule desired to be delivered may be selected for entry into the cells for a plurality of reasons, including, but not intended to be limited to, genetically modifying cells, inducing the secretion of a substance locally or systemically, inducing the production of a substance within a cell, inducing the production of a substance that is embedded in the membrane, or any other purpose known in the art.

The system and method of the invention is further described with the use of the following examples of the expression of luciferase in skin tissue of mice and the gastrocnemius muscle of mice.

Example 1

A plasmid (pCMVLuc), constructed of DNA with a cDNA insert that codes for the enzyme lucerifase, was propagated in the bacterium *E. coli* and then purified using a Quiagen plasmid preparation kit (Quiagen, Valencia, Calif.). The plasmid was suspended in saline at a concentration of 2 mg/ml for use in the experiment. A 50-ml quantity of the plasmid was injected intradermally into the flanks of C57B1/6 mice. Immediately after injection, four surface electrodes were placed on adjacent sides of the injection site and a series of discrete electric pulses with a field strength of 10V/cm were applied to the skin so that current passed through the injected tissue. The duration of these pulses was 1 s. The treated skin was surgically harvested 48 hours later and analyzed using standard methods for luciferase expression. These results, expressed in relative light units, are shown in Table 2.

TABLE 2

Luciferase Expression as a Function of Treatment conditions

| Treatment Conditions | Mean Magnitude of Luciferase Expression |
| --- | --- |
| Injection only | 1,473,712.94 |
| Injection followed by electric field treatment of 10 V/cm, 1 s duration | 7,360,666.54 |

The results of Table 2 indicate that skin treated with the plasmid DNA followed by electric pulses evinced a lucerifase expression that was approximately 5 times higher than samples that were treated with the plasmid alone, clearly indicating that low-electric-field strength pulses with a very long duration facilitated the entry of plasmid DNA into the interior of the skin cells. The duration of the pulses used for these samples was tenfold higher than the maximum duration suggested in the known literature of the art.

Example 2

The procedures in Example 1 were repeated to deliver the luciferase coding plasmid to skin again using different electrical conditions. The results, expressed in relative light units, are shown in Table 3.

TABLE 3

Luciferase Expression as a Function of Treatment conditions

| Treatment Conditions | Mean Magnitude of Luciferase Expression |
| --- | --- |
| Injection of plasmid only | 1,346,832.25 |
| Injection of plasmid followed by electrical treatment 50 V/cm, 200 ms duration | 5,077,201.00 |
| Injection of plasmid followed by electrical treatment 100 V/cm, 200 ms duration | 59,529,447.97 |

The results indicate that using pulses with a field strength of 50 V/cm and a duration of 200 ms yields a luciferase expression that was approximately 3.5 times that of the control animals that received only an injection of the plasmid (no fields were applied). Samples that received 100-V/cm pulses with 200 ms duration had 44 times more luciferase xpression than the control samples. This example indicates that pulse durations well above the highest disclosed by the art have utility for facilitating the delivery of molecules to cells of a target tissues.

Example 3

Plasmid DNA coding for luciferase has also been delivered to murine gascrocnemius muscles. This was carried out by injecting a 50-μl quantity of the plasmid DNA (2 mg/ml) directly into the muscles. A penetrating electrode was then inserted into the muscle tissue that was infused with the plasmid DNA solution and pulsed-electric fields were applied. Forty-eight house after this treatment, the muscles were excised and analyzed for luciferase using standard methods. The resulting data, expressed in relative light units, are given in Table 4.

TABLE 4

Luciferase Expression in Muscle

| Treatment Conditions | Mean Magnitude of Luciferase Expression |
| --- | --- |
| Injection only | 1,393,829 |
| Injection of plasmid followed by electrical treatment 20 V/cm, 1 s duration | 484,134,407 |

The results obtained indicated that muscle treated with the plasmid DNA followed by electric pulses expressed lucerifase approximately 347 times higher than samples that were not treated with the electric pulses. This indicates that the entry of plasmid DNA to the interior of a cell can be effected by long-pulse-duration low-field-strength electrical conditions.

Example 4

Flank skin of mice were shaved and then injected subcutaneously with 50 μl 2 μg/μl plasmid DNA encoding for luciferase. Eight electric pulses were administered in a 4×4 configuration (90° rotation between sets of 4 pulses) at a frequency of 1 Hz with a BTX T830 (BTX Molecular Delivery Systems, Holliston, Mass.) using a 4 plate-electrode wherein each plate was 4 mm wide and all but the inner face was insulated with a clear epoxy. An inner spacer permitted closure of the 4 plates from open position to allow 6 mm between opposite plates. The field strengths and pulse lengths are designated in Table 5 and Table 6. 48 hours after plasmid delivery, animals were humanely euthanized, and the tissue samples were excised and analyzed for luciferase activity.

For luciferase quantitation, the tissue samples were homogenized in buffer [50 mM K3PO4, 1 mM EDTA, 1 mM DTT, 10% glycerol] using a Tissumizer (Tekmar, Cincinnati, Ohio). Extracts were assayed for luciferase activity (Heller, et al., 2000) and quantified using a MLX microtiter plate luminometer (Dynex Technologies, Chantilly, Va.). Activity is expressed in total pg luciferase per tissue sample.

Experiments were performed to evaluate the effect of increasing pulse width on the expression of a plasmid encoding luciferase delivered with in vivo electroporation to the skin of mice. Maintaining the same field strength (100 V/cm) and increasing only the pulse width resulted in increased expression with longer pulse widths as shown in Table 5. Contrary to existing knowledge, when the field strength was reduced, increasing the pulse width resulted in high expression levels (75 V/cm and 150 ms, Table 5). A similar progression can be seen when performing the experiment using established dogma to increase the field strength. As shown in Table 6, increased field strength at the same pulse width results in increased expression. However, it is interesting to note that as the field strength (400 V/cm) is increased to get high expression the level of damage to the tissue is also increased. While with the administration of the long pulses (150 ms) the damage is kept at a low level (Table 7).

TABLE 5

Expression from increasing pulse width

| Delivery | Luciferase Expression (Mean of Means) | Standard Error of the Means | N* |
| --- | --- | --- | --- |
| Eight 100 V/cm 10 ms pulses | 38,818,023 | 31,762,348 | 6 |
| Eight 100 V/cm 20 ms pulses | 63,175,338 | 28,548,687 | 5 |
| Eight 100 V/cm 125 ms pulses | 79,137,048 | 15,028,790 | 3 |

TABLE 5-continued

Expression from increasing pulse width

| Delivery | Luciferase Expression (Mean of Means) | Standard Error of the Means | N* |
|---|---|---|---|
| Eight 100 V/cm 150 ms pulses | 92,114,333 | 28,905,020 | 6 |
| Eight 100 V/cm 200 ms pulses | 96,804,412 | 25,921,640 | 7 |
| Eight 75 V/cm 150 ms pulses | 86,243134 | 40,242,932 | 1 |
| Injection only | 3,160,166 | 3,805,216 | 6 |

*N = number of experiments performed for each condition. Each experiment contained four samples.

TABLE 6

Expression from increasing field strength

| Delivery | Luciferase Expression (Mean of Means) | Standard Error of the Means | N* |
|---|---|---|---|
| Eight 100 V/cm 10 ms pulses | 38,818,023 | 31,762,348 | 6 |
| Eight 200 V/cm 10 ms pulses | 46,693,812 | 34,478,659 | 2 |
| Eight 400 V/cm 10 ms pulses | 69,295,096 | 16,078,861 | 7 |
| Injection only | 3,160,166 | 3,805,216 | 6 |

*N = number of experiments performed for each condition. Each experiment contained four samples.

TABLE 7

Histological assessment of surface damage 48 hours after electroporation using selected electroporation conditions.

| Delivery | Surface Damage[1] |
|---|---|
| No treatment | 0.13 ± 0.30 |
| Injection only | 0.4 ± 0.4 |
| Eight 100 V/cm 20 ms pulses | 1.90 ± 1.50 |
| Eight 100 V/cm 150 ms pulses | 5.12 ± 3.50 |
| Eight 200 V/cm 20 ms pulses | 2.28 ± 1.26 |
| Eight 400 V/cm 10 ms pulses | 20.89 ± 12.98 |

[1] mean ± SD, n = 6

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for facilitating the delivery of a desired molecule into a target tissue comprising the steps of:
   introducing a molecule into a target tissue comprising a cell; and
   applying a continuous electric field having a field strength comprising 200V/cm or less to the target tissue for a duration of 125 ms to 20 minutes to effect a change in porosity of the cell of the target tissue sufficient to facilitate entry of a desired molecule into an interior of the cell.

2. The method recited in claim 1, wherein the duration of the applying step is in a range of 125 ms to 100 sec.

3. The method recited in claim 1, wherein the electric field is a pulse selected from a group of waveforms consisting of square, rectangular, exponentially decaying, exponentially increasing, bipolar, and sinusoidal; waveforms having a non-geometrically characterizable shape; waveforms characterizable by a mathematical function; waveforms characterizable by a mathematical approximation; waveforms with at least one of an AC or a DC offset signal; and waveforms without an AC or a DC offset signal.

4. The method recited in claim 1, wherein the introducing step comprises a step selected from the group consisting of syringe injection, jet injection, oral dosing, transdermal delivery, infusion into tissue, and infusion into a blood vessel.

5. The method recited in claim 1, wherein the target tissue is selected from a group consisting of skin, tumor, muscle, blood, blood vessel, brain, lymph, liver, pancreas, bone, colon, cardiac, lung, breast, testes, cornea, prostate, and intestine.

6. A method for facilitating the delivery of a desired molecule into a target tissue comprising the steps of:
   introducing a molecule into a target tissue comprising a cell; and
   applying a continuous electric field having a field strength comprising 200V/cm or less to the target tissue for a duration of 200 ms to 20 minutes to effect a change in porosity of the cell of the target tissue sufficient to facilitate entry of a desired molecule into an interior of the cell.

7. The method recited in claim 6, wherein the duration of the applying step is in a range of 200 ms to 100 sec.

8. The method recited in claim 6, wherein the electric field is a pulse selected from a group of waveforms consisting of square, rectangular, exponentially decaying, exponentially increasing, bipolar, and sinusoidal; waveforms having a non-geometrically characterizable shape; waveforms characterizable by a mathematical function; waveforms characterizable by a mathematical approximation; waveforms with at least one of an AC or a DC offset signal; and waveforms without an AC or a DC offset signal.

9. The method recited in claim 6, wherein the introducing step comprises a step selected from the group consisting of syringe injection, jet injection, oral dosing, transdermal delivery, infusion into tissue, and infusion into a blood vessel.

10. The method recited in claim 6, wherein the target tissue is selected from a group consisting of skin, tumor, muscle, blood, blood vessel, brain, lymph, liver, pancreas, bone, colon, cardiac, lung, breast, testes, cornea, prostate, and intestine.

* * * * *